(12) United States Patent
Swoyer et al.

(10) Patent No.: US 9,089,693 B2
(45) Date of Patent: Jul. 28, 2015

(54) LEAD POSITIONING AND FINNED FIXATION SYSTEM

(75) Inventors: John Swoyer, Blaine, MN (US); James Finley, Minneapolis, MN (US); Lawrence Kane, Roseville, MN (US)

(73) Assignee: Greatbatch Ltd., Clarence, NY (US)

( * ) Notice: Subject to any disclaimer, the term of this patent is extended or adjusted under 35 U.S.C. 154(b) by 569 days.

(21) Appl. No.: 13/537,341

(22) Filed: Jun. 29, 2012

(65) Prior Publication Data

US 2014/0005675 A1    Jan. 2, 2014

(51) Int. Cl.
*A61N 1/05* (2006.01)
*A61N 1/36* (2006.01)

(52) U.S. Cl.
CPC ............ *A61N 1/0551* (2013.01); *A61N 1/3605* (2013.01); *A61N 1/36053* (2013.01)

(58) Field of Classification Search
CPC .. A61N 1/0558; A61N 1/0551; A61N 1/3605
USPC .................................. 607/115–117; 606/129
See application file for complete search history.

(56) References Cited

U.S. PATENT DOCUMENTS

| 7,904,149 | B2 | 3/2011 | Gerber |
| 2003/0045919 | A1* | 3/2003 | Swoyer et al. ............... 607/122 |
| 2008/0103572 | A1 | 5/2008 | Gerber |
| 2008/0103574 | A1 | 5/2008 | Gerber |

\* cited by examiner

*Primary Examiner* — Katherine M Shi
(74) *Attorney, Agent, or Firm* — Michael P. Horvath

(57) ABSTRACT

A therapy assembly configured for at least partial insertion in a living body. At least one fixation structure is attached to the therapy delivery element proximate the electrodes. The fixation structure is configured to collapse radially inward and wrap circumferentially around the therapy delivery element to a collapsed configuration when inserted into a lumen of an introducer. The fixation structures deploy to a deployed configuration when the introducer is retracted. The fixation structure includes major surfaces generally parallel with, and extending radially outward from, a central axis of the therapy delivery element, proximal edge surface oriented toward the proximal end, and a distal edge surface oriented toward the distal end. The proximal and distal edge surfaces provide generally symmetrical resistance to displacement of the therapy delivery element within the living body in either a proximal direction or a distal direction along the central axis.

19 Claims, 14 Drawing Sheets

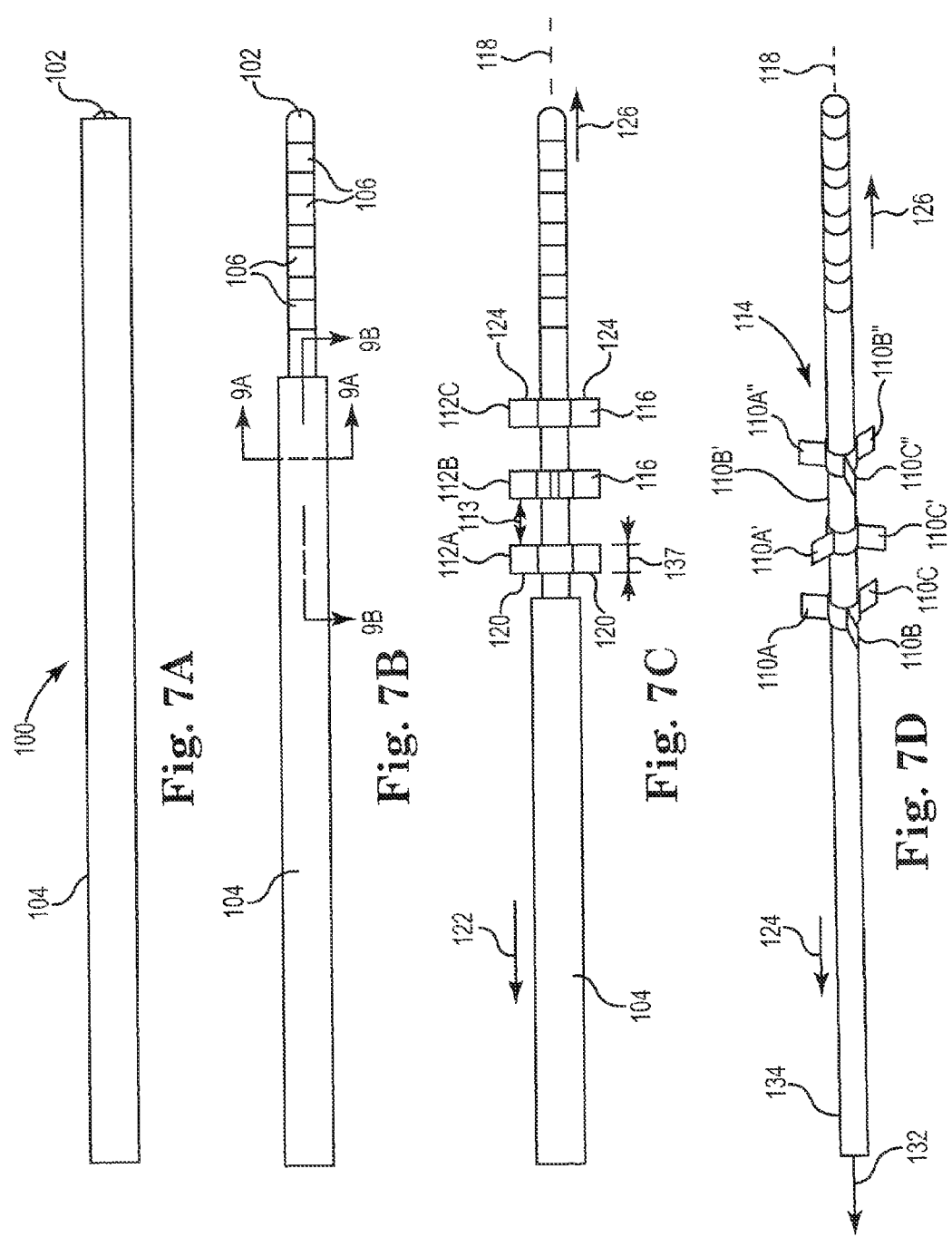

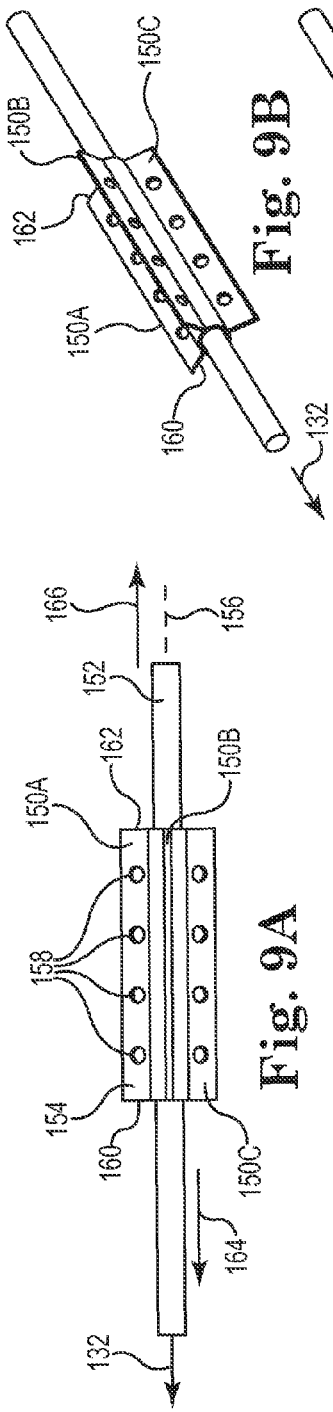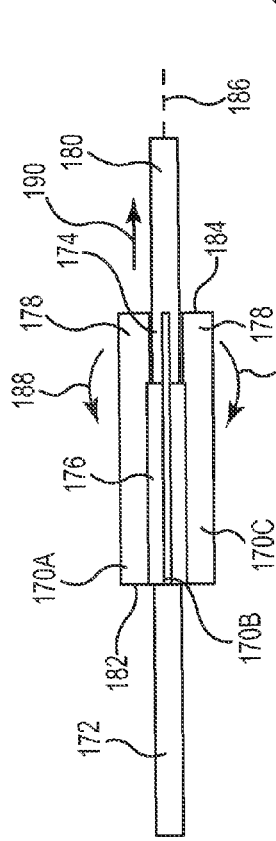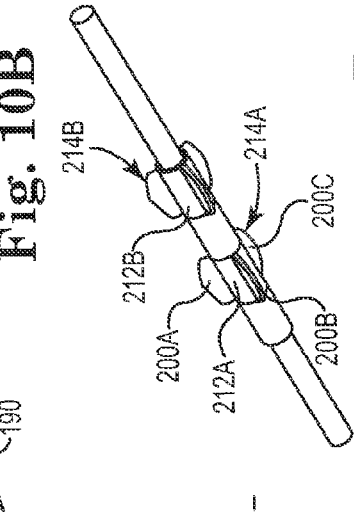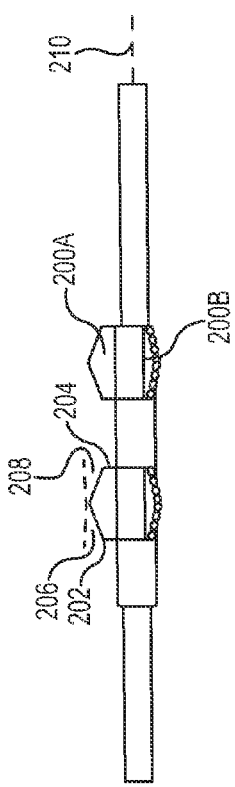

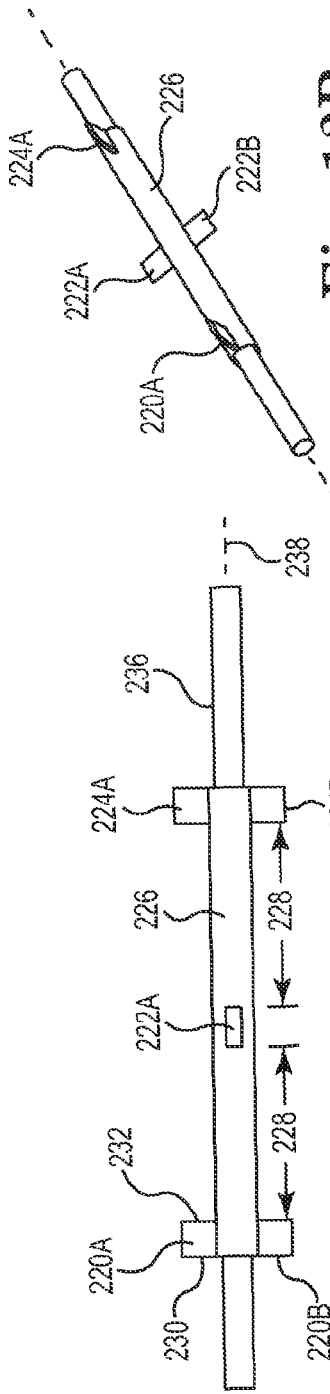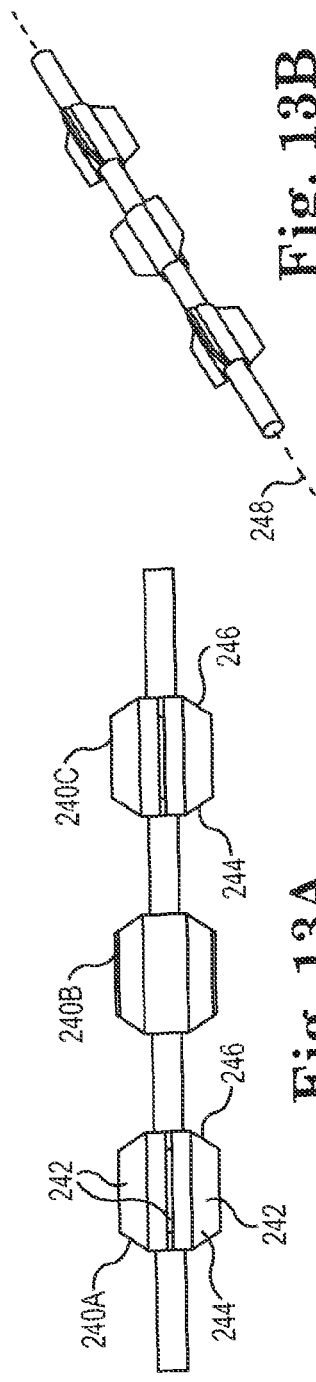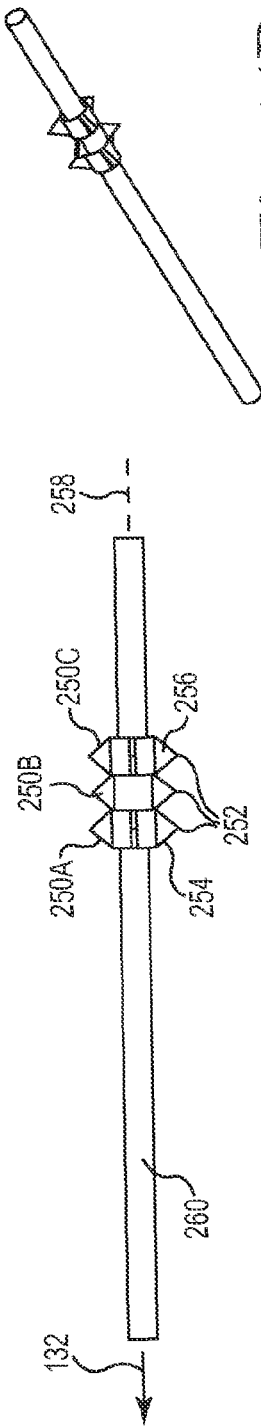

LEAD POSITIONING AND FINNED FIXATION SYSTEM

FIELD

The present disclosure is directed to a method and apparatus that allows for stimulation of body tissue, particularly nerves. More specifically, the implantable medical electrical lead includes at least one axially oriented fixation structure with leading and trailing edge surfaces to provide generally symmetrical bi-axial fixation.

BACKGROUND

Implantable medical electronics devices consist of an implanted pulse generator that is used to provide electrical stimulation to certain tissues and an implantable lead or leads that are used to transmit the electrical impulse to the targeted tissues. Examples include cardiac pacemaking, and a number of related applications for cardiac rhythm management, treatments for congestive heart failure, and implanted defibrillators. Other applications for implantable pulse generators include neurostimulation with a wide range of uses such as pain control, nervous tremor mitigation, incontinence treatment, epilepsy seizure reduction, vagus nerve stimulation for clinical depression, and the like.

Despite various suture fixation devices, nerve stimulation leads can be dislodged from the most efficacious location due to stresses placed on the lead by the ambulatory patient. A surgical intervention is then necessary to reposition the electrode and affix the lead. The implantable pulse generator ("IPG") is programmed to deliver stimulation pulse energy to the electrode providing the optimal nerve response. The efficacy of the selected electrode can fade over time due to dislodgement or other causes.

Physicians spend a great deal of time with the patient under a general anesthetic placing the small size stimulation electrodes relative to the target nerves. The patient is thereby exposed to the additional dangers associated with extended periods of time under a general anesthetic. Movement of the lead, whether over time from suture release or during implantation during suture sleeve installation, is to be avoided. As can be appreciated, unintended movement of any object positioned proximate a nerve may cause unintended nerve damage. Moreover reliable stimulation of a nerve requires consistent nerve response to the electrical stimulation that, in turn, requires consistent presence of the stimulation electrode proximate the target nerve. On the other hand, if the target nerve is too close to the electrode, inflammation or injury to the nerve can result, diminishing efficacy and possibly causing patient discomfort.

Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known in the art as exemplified by U.S. Pat. Nos. 3,902,501, 3,939,843, 4,033,357, 4,236,529, 4,269,198, 4,301,815, 4,402,328, 4,409,994, and 4,883,070. Such tined leads typically employ tines that extend outwardly and proximally from a band proximal to a distal tip pace/sense electrode and that catch in natural trabecular interstices when the distal tip electrode is advanced into the a trial appendage or the ventricular apex.

Certain spinal cord stimulation leads have been proposed employing tines and/or vanes as stand-offs to urge the stimulation electrode in the epidural space toward the spinal cord as disclosed in U.S. Pat. Nos. 4,590,949 and 4,658,535, for example, and to stabilize the stimulation electrode in the epidural space as disclosed in U.S. Pat. No. 4,414,986, for example.

Stimulation leads for certain pelvic floor disorders have been proposed with a fixation mechanism that includes a plurality of tine elements arrayed in a tine element array along a segment of the lead proximal to the stimulation electrode array, such as for example in U.S. Pat. Nos. 6,999,819; 7,330,764; 7,912,555; 8,000,805; and 8,036,756. Each tine element includes a plurality of flexible, pliant, tines. The tines are configured to be folded inward against the lead body when fitted into and constrained by the lumen of an introducer.

Peripheral nerve field stimulation ("PNFS") involves delivery of stimulation to a specific peripheral nerve via one or more electrodes implanted proximate to or in contact with a peripheral nerve, such as disclosed in U.S. Pat. Publication No. 2009/0281594. PNFS may be used to deliver stimulation to, for example, the vagal nerves, cranial nerves, trigeminal nerves, ulnar nerves, median nerves, radial nerves, tibial nerves, and the common peroneal nerves. When PNFS is delivered to treat pain, one or more electrodes are implanted proximate to or in contact with a specific peripheral nerve that is responsible for the pain sensation.

During the implantation procedure the surgeon selectively activates the electrodes to test nerve response (also referred to as "mapping") to determine optimal lead position. Fixation structures on the lead are typically restrained by the introducer during the mapping process. Optimal lead placement must be achieved before deploying any fixation structures.

Prior art fixation strategies include barbed or angled structures that provide greater fixation in one direction along the central axis of the lead. For example, U.S. Pat. No. 7,684,873 (Gerber) and U.S. Pat. No. 6,999,819 (Swoyer et al.) both disclose fixation tines angled with respect to the central axis of the lead. This approach tends to provide excess fixation in the proximal direction, complicating lead removal, and inadequate fixation in the distal direction.

The asymmetry in these fixation approaches creates greater risk of the lead being inadvertently displaced in the distal direction, such as by patient movement, rather than in the proximal direction. For example, if the lead is subjected to cyclical push-pull forces, the angled tines provide a ratcheting-action that favors displacement in the distal direction over the proximal direction. Over time, the lead will tend to migrate in the distal direction, resulting in misplacement of the electrodes relative to the target nerve tissue.

BRIEF SUMMARY

The present disclosure is directed to a therapy assembly configured for at least partial insertion in a living body. The therapy assembly includes a therapy delivery element with a proximal end having a plurality of electrical contacts configured to electrically couple with an implantable pulse generator, and a distal end with a plurality of electrodes that are electrically coupled to the electrical contacts at the proximal end. An introducer with a lumen configured to receive the therapy delivery element is provided. At least one fixation structure is attached to the therapy delivery element near the electrodes. The fixation structure is configured to collapse radially inward and wrap circumferentially around the therapy delivery element to a collapsed configuration when inserted into the lumen of the introducer. The at least one fixation structure deploys to a deployed configuration when the introducer is retracted. The fixation structure includes major surfaces generally parallel with, and extending radially outward from, a central axis of the therapy delivery element. The at least one fixation structure also includes a proximal edge surface oriented toward the proximal end, and a distal edge surface oriented toward the distal end. The proximal and distal edge surfaces provide generally symmetrical resistance to displacement of the therapy delivery element within the living body in either a proximal direction or a distal direction along the central axis.

In one embodiment, the at least one fixation structure includes a plurality of fixation structures that wrap circumferentially around the therapy delivery element in a non-overlapping configuration when inserted into the lumen of the introducer. A plurality of fixation assemblies can be axially spaced along the therapy delivery element. The fixation assemblies preferably include a plurality of fixation structures. In one embodiment, the fixation assemblies are rotationally offset so the proximal and distal edge surfaces of the fixation structures on at least two fixation assemblies are out-of-plane. The axial spacing between the fixation assemblies is typically in a range of between about 0.050 inches to about 0.150 inches.

The fixation structures preferably have a radial dimension in a range between about 0.030 to about 0.150, and more preferably in a range between about 0.045 inches to about 0.065 inches, and an axial dimension in a range of about 0.050 inches to about 0.200 inches. A therapy delivery element with the present fixation structures exhibit a pullout-force from the living body in a range of between about 0.50 pounds to about 3.00 pounds.

The fixation structure can be bonded directly to the therapy delivery element or attached to a sleeve that is bonded to the therapy delivery element. The at least one fixation structure optionally includes at least one edge surface oriented at an angle relative to a central axis of the therapy delivery element. The at least one fixation structure can be rectangular, trapezoidal, circular, curvilinear, or triangular.

In one embodiment, the fixation structures include at least four proximal edge surfaces and four distal edge surfaces. The proximal edge surfaces preferably have a total surface area within about +/−20% or less than a total surface area of the distal edge surfaces. The fixation structure provides a resistance to a displacement force applied to the therapy delivery element in the proximal direction is within about +/−20% or less to resistance to a displacement force applied in the distal direction.

The present disclosure is also directed to a method of implanting a therapy assembly in a living body. The method includes inserting an introducer adjacent into the living body near an implantation site. A distal end of a therapy delivery element is then inserted into a lumen in the introducer to collapse radially inward fixation structures attached to the therapy delivery element near the distal end. The therapy delivery element is rotated slightly during insertion into the introducer to wrap the fixation structures circumferentially around the therapy delivery element to a collapsed configuration. Placement of the therapy delivery element in the living body is confirmed. The introducer is retracted out of the living body to deploy the fixation structures to a deployed configuration. The fixation structures include major surfaces generally parallel with, and extending radially outward from a central axis of the therapy delivery element, a proximal edge surface oriented toward the proximal end of the therapy delivery element, and a distal edge surface oriented toward the distal end of the therapy delivery element.

The method includes electrically coupling electrical contacts at a proximal end of the therapy delivery element with an implantable pulse generator. The method includes the step of engaging the proximal and distal edge surfaces with tissue in the living body to provide generally symmetrical resistance to displacement of the therapy delivery element in either a proximal direction or a distal direction along the central axis.

In one embodiment, the method includes wrapping the fixation structures circumferentially around the therapy delivery element in a non-overlapping configuration when in the collapsed configuration. The method optionally includes axially spacing a plurality of fixation assemblies along the therapy delivery element. The plurality of fixation assemblies on the therapy delivery element can be rotationally offset so the proximal and distal edge surfaces of the fixation structures on at least two fixation assemblies are out-of-plane. In one embodiment, the plurality of fixation structures on the therapy delivery element are arranged with at least four proximal edge surfaces and four distal edge surfaces.

BRIEF DESCRIPTION OF THE DRAWINGS

FIG. 7A illustrates a therapy assembly in an introducer in accordance with an embodiment of the present disclosure.

FIG. 7B illustrates the introducer of FIG. 7A retracted to expose the electrodes in accordance with an embodiment of the present disclosure.

FIG. 7C illustrates the introducer of FIG. 7A retracted to deploy fixation structures in accordance with an embodiment of the present disclosure.

FIG. 7D illustrates the introducer of FIG. 7A removed in accordance with an embodiment of the present disclosure.

FIGS. 9A and 9B are side and perspective views of a therapy delivery element with fixation structures in accordance with an embodiment of the present disclosure.

FIGS. 10A and 10B are side and perspective views of a therapy delivery element with free floating fixation structures in accordance with an embodiment of the present disclosure.

FIGS. 11A and 11B are side and perspective views of a therapy delivery element with trapezoidal fixation structures in accordance with an embodiment of the present disclosure.

FIGS. 12A and 12B are side and perspective views of a therapy delivery element with longitudinally spaced and rotationally offset fixation structures on a single sleeve in accordance with an embodiment of the present disclosure.

FIGS. 13A and 13B are side and perspective views of a therapy delivery element with longitudinally spaced and rotationally offset trapezoidal fixation assemblies in accordance with an embodiment of the present disclosure.

FIGS. 14A and 14B are side and perspective views of a therapy delivery element with triangular fixation structures in accordance with an embodiment of the present disclosure.

The drawings are not necessarily to scale. Like numbers refer to like parts or steps throughout the drawings.

DETAILED DESCRIPTION OF SOME EMBODIMENTS

The description that follows highlights spinal cord stimulation (SCS) system, the treatment of pelvic floor disorders, and peripheral nerve field stimulation (PNFS). However, it is to be understood that the disclosure relates to any type of implantable therapy delivery system with one or more therapy delivery elements with one or more electrodes or sensors. For example, the present disclosure may be used as part of a pacemaker, a defibrillator, a cochlear stimulator, a retinal stimulator, a stimulator configured to produce coordinated limb movement, a cortical stimulator, a deep brain stimulator, microstimulator, or in any other neural stimulator configured to treat sleep apnea, shoulder sublaxation, headache, etc.

In another embodiment, one or more of the therapy delivery elements may be a fluid or drug delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be a medical electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
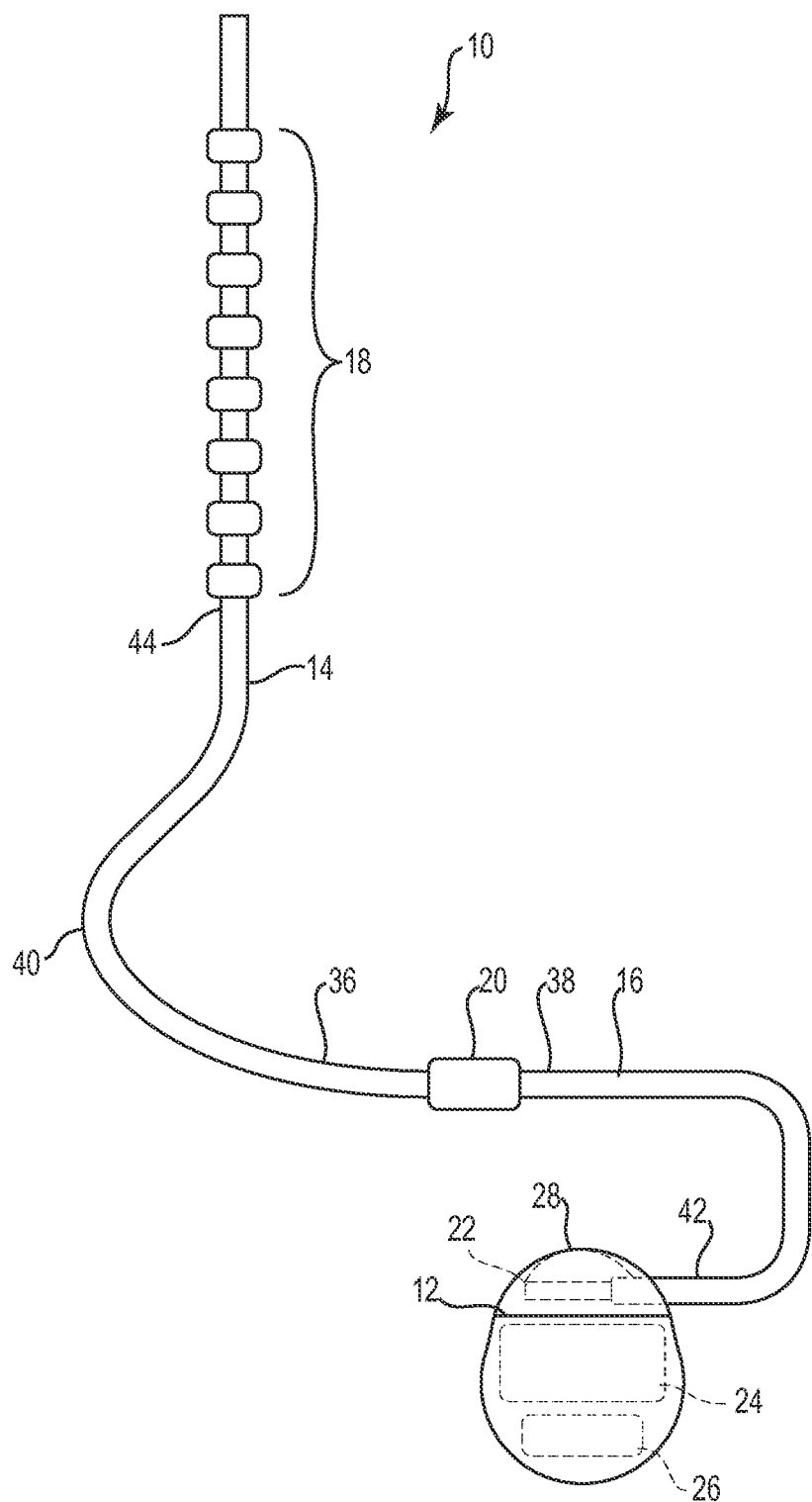
FIG. 1 is a schematic illustration of a therapy delivery system.

FIG. 1 illustrates a generalized therapy delivery system 10 that may be used in stimulation applications. The therapy delivery system 10 generally includes an implantable pulse generator 12 ("IPG"), an implantable therapy delivery element 14, which carries an array of electrodes 18 (shown exaggerated for purposes of illustration), and an optional implantable extension lead 16. The electrodes 18 are typically rings or hollow cylinders that extend around a portion of the circumference of the therapy delivery element 14. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter ranging between about 0.03 inches to about 0.07 inches and a length ranging between about 30 cm to about 90 cm for spinal cord stimulation applications. The lead body 40 may include a suitable electrically insulative coating, such as, a polymeric material (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2A:
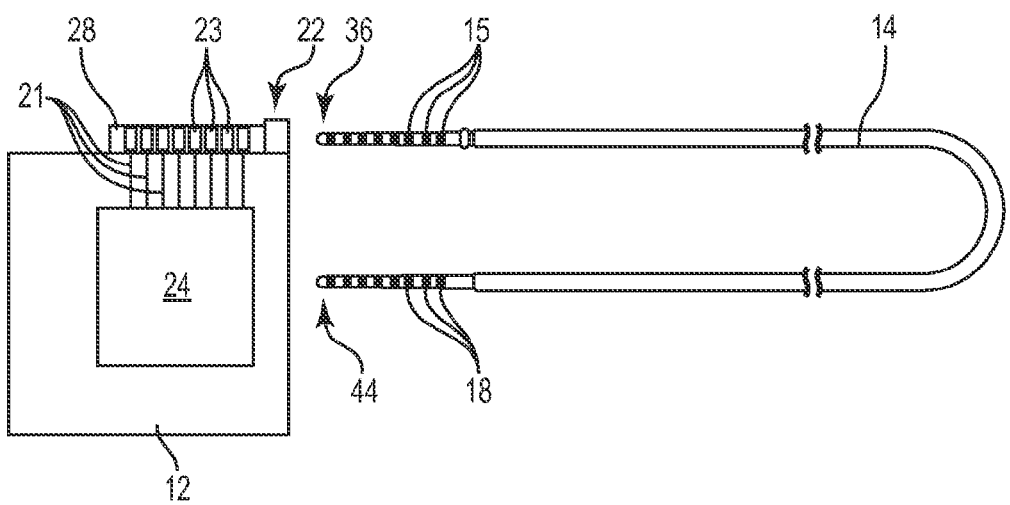
FIG. 2A is a schematic illustration of an implantable pulse generator and a therapy delivery element in accordance with an embodiment of the present disclosure.

FIG. 2A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22. In the embodiment illustrated in FIGS. 2A and 2B, the therapy delivery element 14 forms a medical electrical lead.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can be configured to independently deliver electrical impulses to each of the electrodes 18.

Figure 2B:
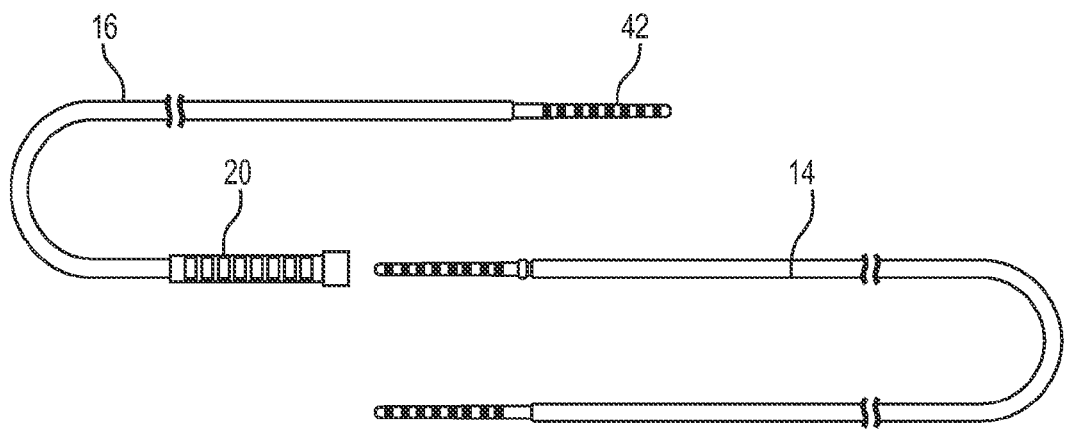
FIG. 2B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 2B. The connector 20 at the distal end 38 of the lead extension 16 preferably includes a plurality of the contacts 23 configured in a manner similar to the connector assembly 22.

Figure 3:
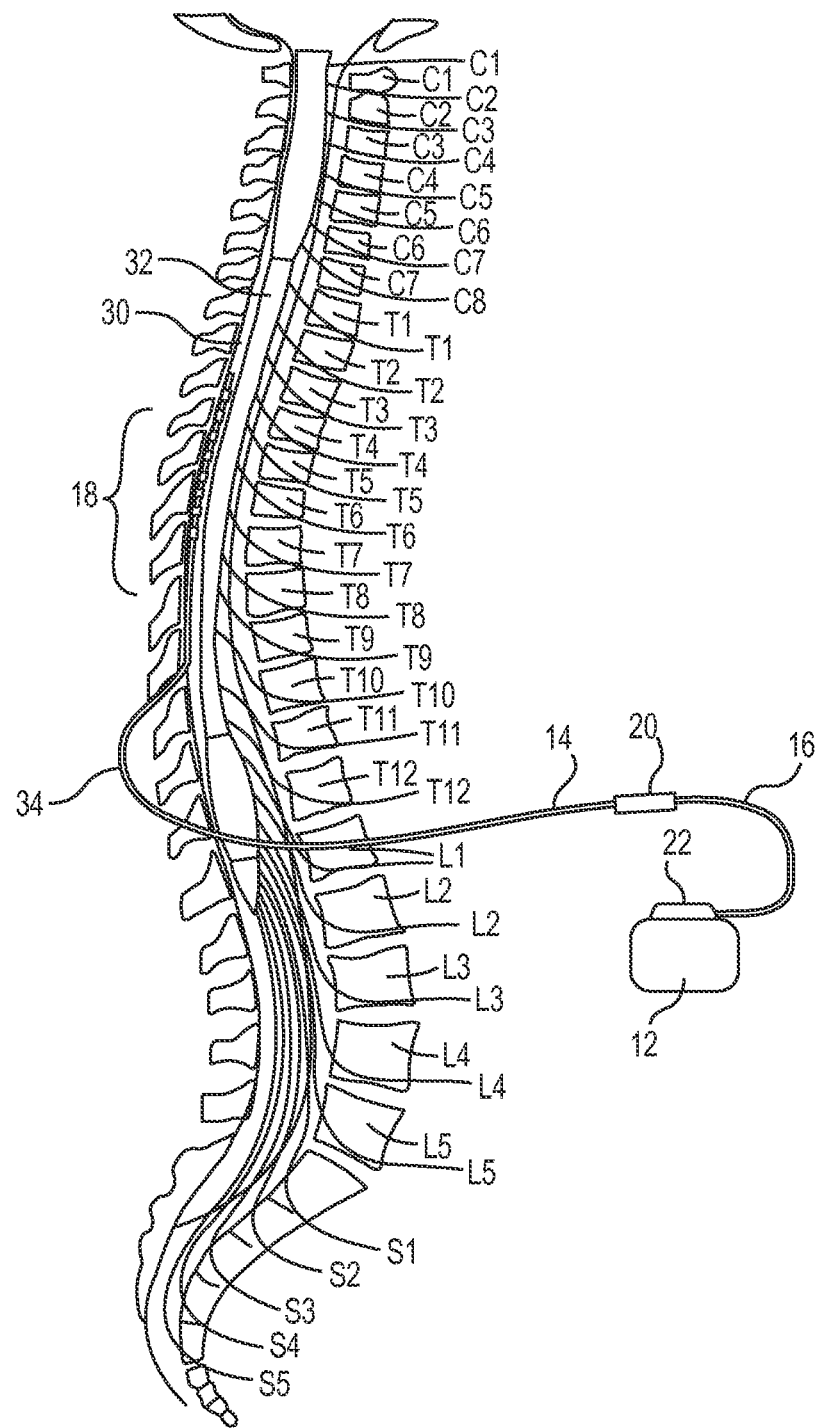
FIG. 3 is a schematic illustration of a therapy delivery system for spinal cord stimulation in accordance with an embodiment of the present disclosure.

FIG. 3 illustrates the therapy delivery element 14 used for spinal cord stimulation (SCS) implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as proximate the sacral nerves.

Figure 4:
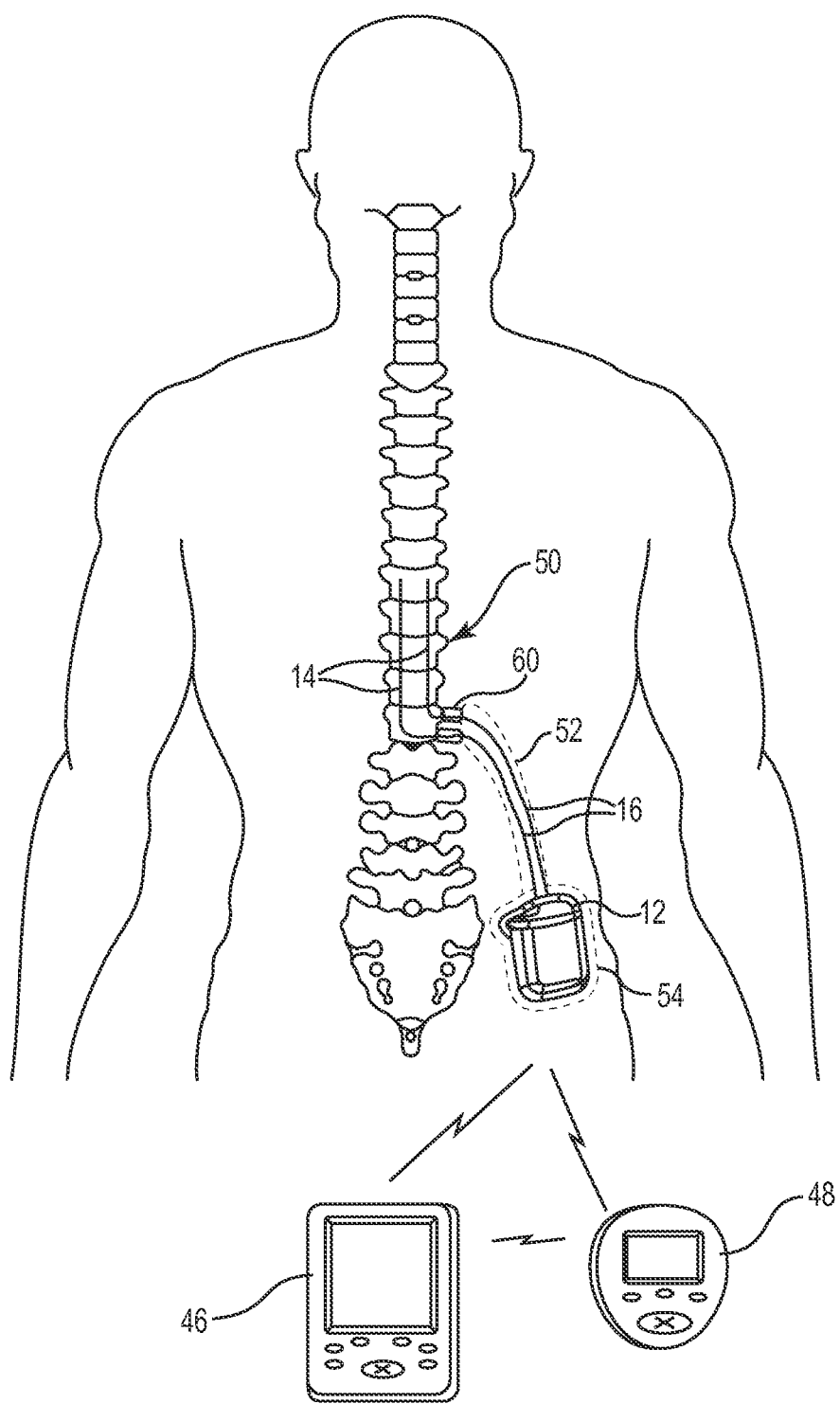
FIG. 4 is an alternate illustration of an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 4. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 4, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" may be used interchangeably, unless context indicates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 5:
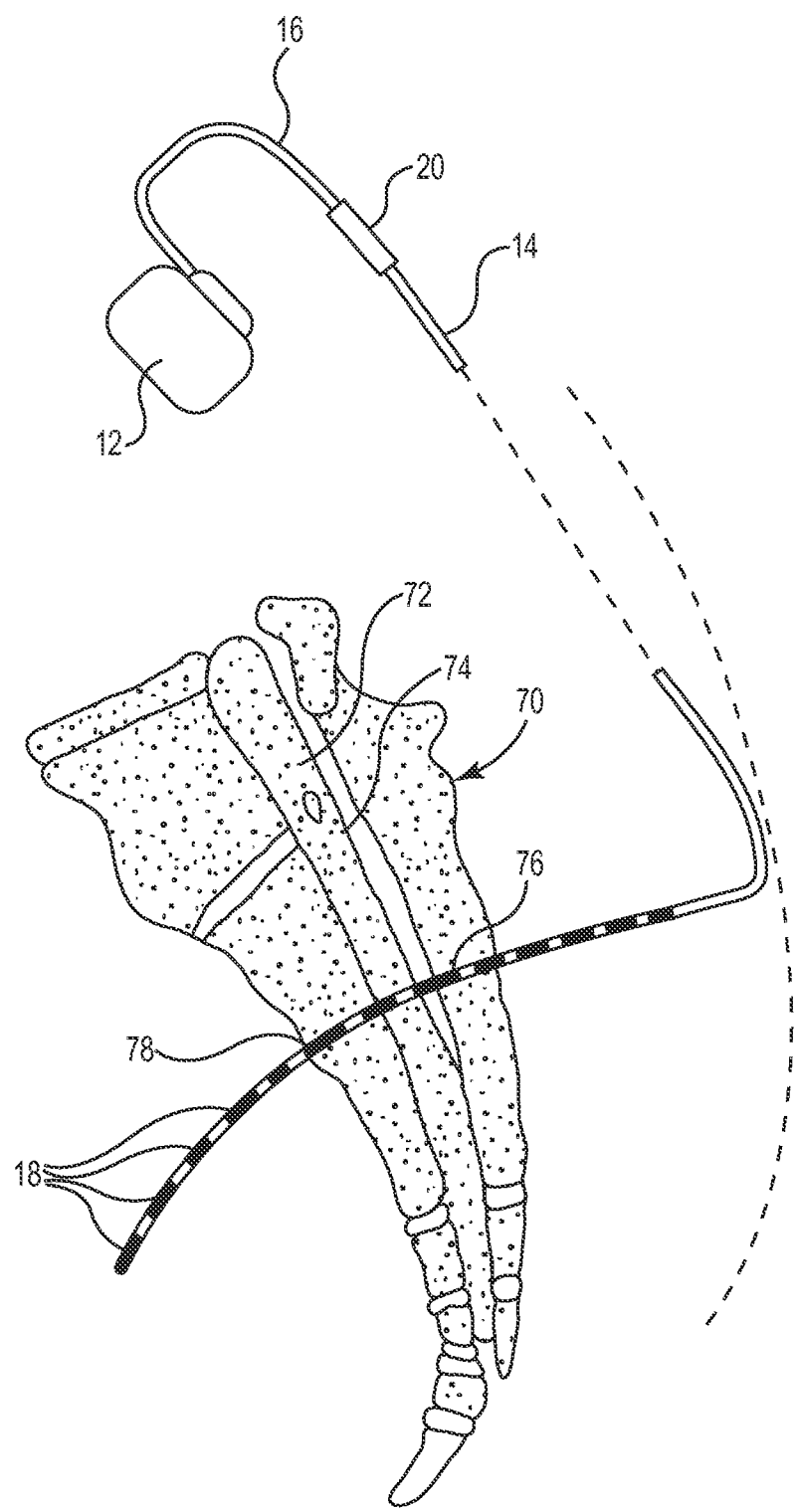
FIG. 5 is a schematic illustration of a therapy delivery system for treating pelvic floor disorders in accordance with an embodiment of the present disclosure.

FIG. 5 illustrates the therapy delivery element 14 used for pelvic floor disorders such as, urinary incontinence, urinary urge/frequency, urinary retention, pelvic pain, bowel dysfunction (constipation, diarrhea), erectile dysfunction, are bodily functions influenced by the sacral nerves. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles 72 within the sacrum 70. The sacrum 70, generally speaking, is a large, triangular bone situated at the lower part of the vertebral column, and at the upper and back part of the pelvic cavity. The spinal canal 74 runs throughout the greater part of the sacrum 70. The sacrum is perforated by the posterior sacral foramina 76 and anterior sacral foramina 78 that the sacral nerves 72 pass through.

Specifically, urinary incontinence is the involuntary control over the bladder that is exhibited in various patients. The therapy delivery element 14 is percutaneously implanted through the foramina 76, 78 of the sacral segment S3 for purposes of selectively stimulating the S3 sacral nerve 72. Stimulation energy is applied through the lead 14 to the electrodes 18 to test the nerve response. The electrodes 18 are moved back and forth to locate the most efficacious location, and the lead 14 is then secured by suturing the lead body to subcutaneous tissue posterior to the sacrum 70 and attached to the output of a neurostimulator IPG 12.

Figure 6:
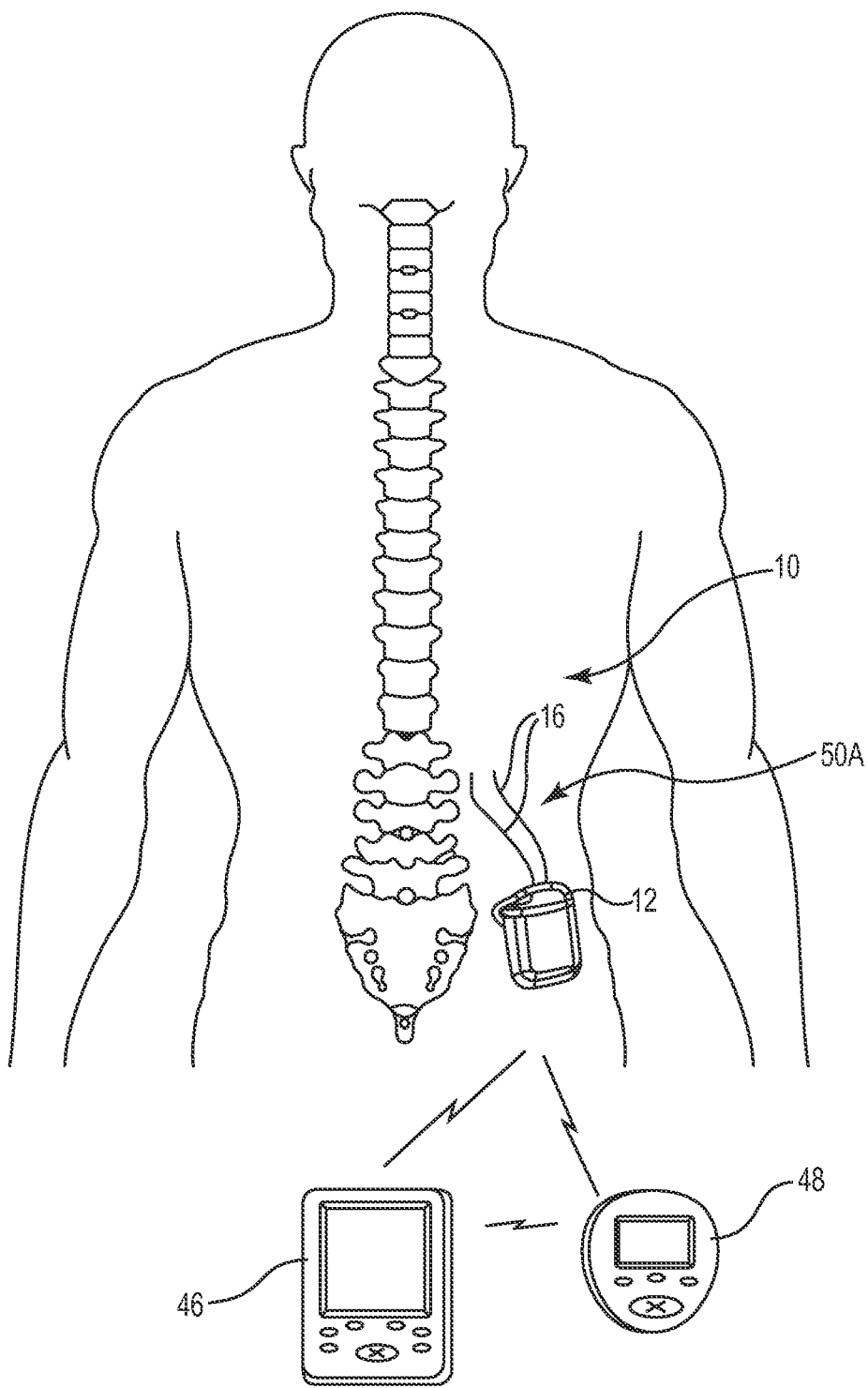
FIG. 6 is a schematic illustration of a therapy delivery system for peripheral nerve stimulation in accordance with an embodiment of the present disclosure.

FIG. 6 illustrates the therapy delivery element 14 used for delivering peripheral nerve field stimulation (PNFS) to a patient. Therapy delivery element 14 delivers PNFS from the implantable pulse generator 12 to the tissue of patient at target location 50A where patient experiences pain. Clinician programmer 46 and patient programmer 48 may communicate via wireless communication with the implantable pulse generator 12.

Therapy delivery element 14 may be implanted within or between, for example, intra-dermal, deep dermal, or subcutaneous tissue of patient at the location 50A where patient experiences pain. Subcutaneous tissue includes skin and associated nerves, and muscles and associated nerves or muscle fibers. In the illustrated example, location 50A is a region of the lower back. In other examples, the therapy delivery element 14 may extend from implantable pulse generator 12 to any localized area or dermatome in which patient experiences pain, such as various regions of the back, the back of the head, above the eyebrow, and either over the eye or under the eye, and may be used to treat failed back surgery syndrome (FBBS), cervical pain (e.g., shoulder and neck pain), facial pain, headaches supra-orbital pain, inguinal and pelvic pain, chest and intercostal pain, mixed pain (e.g., nociceptive and neuropathic), visceral pain, neuralgia, peroneal pain, phantom limb pain, and arthritis.

FIGS. 7A and 7B illustrate a therapy assembly 100 including a therapy delivery element 102 located in lumen 105 (see FIG. 8C) of introducer 104 in accordance with an embodiment of the present disclosure. The therapy delivery element 102 includes a plurality of ring electrodes 106 near distal end 108. The ring electrodes 106 wrap around the periphery of the distal end 108 so the radial orientation of the therapy delivery element 102 does not impact its ability to simulate the target nerve tissue during testing and implantation.

Figure 15:
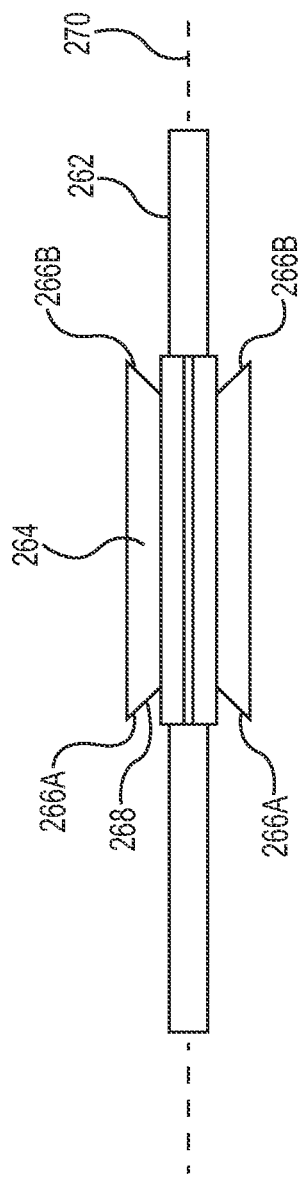
FIG. 15 is a side view of a therapy delivery element with angled fixation surfaces in accordance with an embodiment of the present disclosure.
Figure 16:
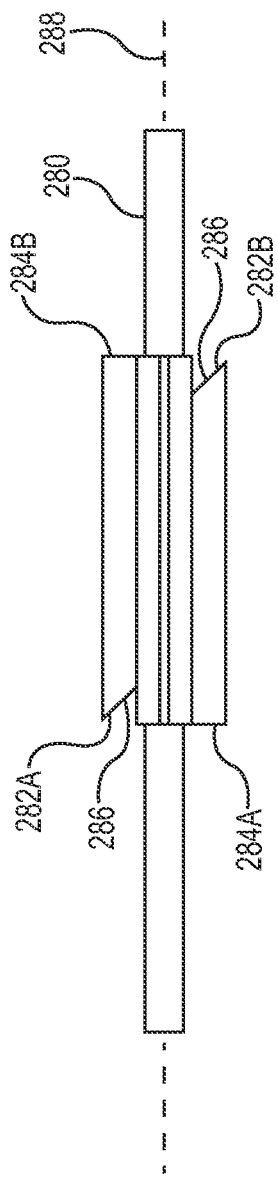
FIG. 16 is a side view of a therapy delivery element with hybrid fixation surfaces in accordance with an embodiment of the present disclosure.

In use, the surgeon positions the therapy assembly 100 illustrated in FIG. 7B adjacent to the target nerve tissue using known techniques (see e.g., FIGS. 15 and 16). The energized electrodes 106 stimulate the adjacent nerve tissue in order to map the nerve response and better position the therapy delivery element 102.

As illustrated in FIGS. 7C and 7D, once the mapping process is completed and the surgeon is satisfied with placement of the therapy delivery element 102, the introducer 104 is withdrawn to release fixation structures 110A, 110B, 110C, 110A', 110B', 110C', 110A", 110B", 110C" ("110"), from one or more fixation assemblies 112A, 112B, 112C ("112"). Each of the fixation structures 110 expands radially outward from central axis 118 to a deployed configuration 114. The fixation assemblies 112 are longitudinally spaced along the therapy delivery element 102. The axial spacing 113 between each fixation assembly 112 can be the same or different.

In the illustrate embodiment, the fixation structures 110 are generally planar structures with major surfaces 116 that are parallel to, and extend generally radially out from, central axis 118 of the therapy delivery element 102. The axial orientation of the fixation structures 110 when in the deployed configuration 114 facilitates subsequent removal of the therapy delivery element 102.

Each fixation structure 112 includes a proximal edge surface 120 that resists displacement of the therapy delivery element 102 along the central axis 118 in a proximal direction 122, and a distal edge surface 124 that resists displacement in a distal direction 126. Friction of the major surfaces 116 also resists displacement in both directions 122, 126 along the central axis 118.

The total surface area of the proximal edge surfaces 120 is preferably within about +/−20% or less than the total surface area of the distal edge surfaces 124, so that the fixation structures 110 provide generally symmetrical fixation of the therapy delivery element 102 in a living body. As used herein, "generally symmetrical resistance to displacement" refers to resistance to a displacement force applied to a therapy delivery element in a proximal direction along a central axis that is within about +/−20% or less to a resistance to a displacement force applied in the distal direction along the central axis.

The fixation structures 112 are preferably attached to sleeve 130, which is subsequently bonded to the therapy delivery element 102. As used herein "bonded" or "bonding" refers to adhesive bonding, solvent bonding, ultrasonic welding, thermal bonding, and a variety of other techniques. In another embodiment, the fixation structures 112 are discrete elements that are bonded directly to the therapy delivery element 102.

The fixation structures 112 are can be made from a variety of bio-compatible polymeric or metal materials, such as for example, polyethylene terephthalate (PET), Nylon, polyether ether ketone (PEEK), polyproylene, high-performance polyethylenes, bioabsorbale polymers, such as polyglutamic acid (PGA), poly-L-lactide (PLLA), or polycaprolactone (PCL), urethanes such as Tecothane®, silicone, Nitinol, stainless steel, MP35N, titanium, or any combination of these materials. Tecothane® aromatic polyether-based thermoplastic polyurethanes are resins which exhibit solvent resistance and biostability over a wide range of hardness. The introducer 104 are can be made from a variety of flexible bio-compatible polymeric or metal materials, such as for example, polyethylene terephthalate (PET), Nylon, polyproylene, high-performance polyethylenes, urethane, silicone, or any combination of these materials.

As best illustrated in FIG. 7D, the fixation assemblies 112 can be both rotationally and axially offset from each other. For example, the fixation assembly 112B is rotated about 60 degrees relative to the fixation assemblies 112A, 112C. Edge surfaces 120, 124 of the fixation structures 110A, 110B, 110C, 110A", 110B", 110C" on the fixation assemblies 112A, 112C are rotationally offset from the edge surfaces 120, 124 on the fixation structures 110A', 110B', 110C on the fixation assembly 112B. The major surfaces 116 and the edge surfaces 120, 124 of the fixation structures 110A and 110A" on the fixation assemblies 110A, 110C are generally in the same plane. The same is also true for the fixation structures 110B and 110B" and the fixation structures 110C and 110C".

The edge surfaces 120, 124 and major surfaces 116 of the fixation structure 110A' on the fixation assembly 112B, however, are not in the same plane (i.e., out-of-plane) with the corresponding fixation structures 110A, and 110A" on the fixation assemblies 112A, 112C. Consequently, the fixation structures 112 provide nine proximal edge surfaces 120 that resist displacement in direction 122 and nine distal edge surfaces 124 that resist displacement in direction 126.

Figures 8A, 8B:
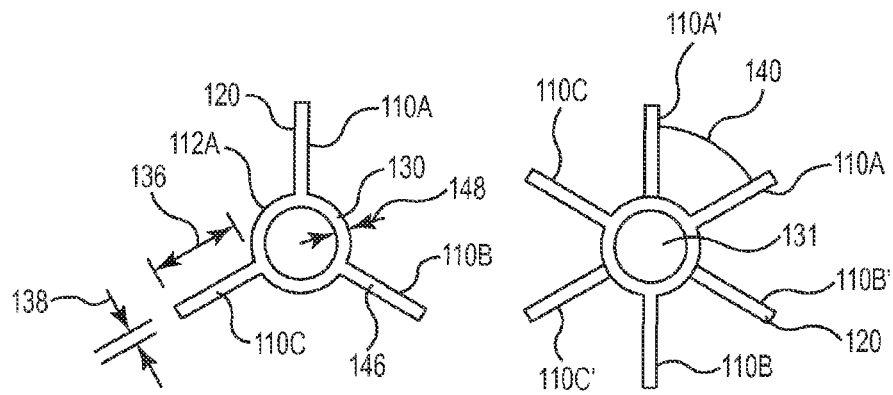
FIG. 8A is an end view of a fixation assembly in accordance with an embodiment of the present disclosure.
FIG. 8B is an end view of a plurality of fixation assemblies rotationally offset in accordance with an embodiment of the present disclosure.

FIG. 8A is an axial view from either end of the fixation assembly 112A illustrated in FIGS. 7C and 7D. Each of the fixation structures 110 includes a radial dimension 136, axial dimension 137 (see FIG. 7C), and thickness 138. The radial dimension 136 and the thickness 138 define surface area 146 of the edge surfaces 120. Since the fixation structures 110 are symmetrical, the distal edge surfaces 124 have the same surface area 146.

FIG. 8B is an axial view of the fixation assemblies 112A, 112B as configured in FIG. 7D, with fixation assembly 112B rotationally offset at angle 140 from the fixation assembly 112A. In the illustrated embodiment the angle 140 is about 60 degrees, although the actual angle can vary. This configuration doubles the number of edge surfaces 120, 124 resisting displacement in directions 122, 126, respectively.

In the illustrated embodiment, the edge surfaces 120, 124 are perpendicular to the central axis 118 and have about the same surface area. The fixation structures 110 are generally symmetrical. As a result, the fixation structures 110 provide generally symmetrical resistance to displacement of the therapy delivery element 102 in either the proximal direction 124 or the distal direction 126. The present fixation structure 110 provides bi-directional axial fixation using opposite edge surfaces of a single structure.

The fixation structures 110 and the sleeve 130 are preferably extruded and then cut to length. The fixation structures 110 are optionally constructed from a radiopaque filled material. Any number of fixation structures 110 can be used, but typically there are about 2 to about 12. Any number of fixation assemblies 112 can be used, but typically there are about 2 to about 5.

The sleeve 130 typically has an inside diameter 131 corresponding to outside diameter of the therapy delivery element 102. The sleeve 130 has a thickness 148 in a range between about 0.005 inches to about 0.015 inches, or about 0.008 inches. The fixation structures 110 can have a radial dimension 136 in a range between about 0.050 inches to about 0.100 inches. Axial dimensions 137 are typically in a range of between about 0.030 inches to about 0.500 inches. The axial spacing 113 between adjacent fixation assemblies 110 is typically in a range of between about 0.050 inches to about 0.200 inches.

In some preferred embodiments, three discrete fixation assemblies 112 as disclosed in FIG. 7D with three fixation structures 110 arranged at 120 degree intervals were bonded to a therapy delivery element 102. The middle of the three fixation assemblies 112 was rotationally offset by 60 degrees. The fixation assemblies 112 were constructed from Tecothane®. Each fixation structure 110 had a thickness of about 0.008 inches, a radial dimension 136 of about 0.055 inches, and an axial dimension 137 in a range of about 0.070 inches to about 0.200 inches. The resulting edge surfaces 120, 124 have an area of about 0.0004 square-inches. The axial spacing was in a range of between about 0.110 inches to about 0.135 inches. The resulting therapy delivery elements 102 exhibited a pull-out force 132 from tissue in a range of between about 0.920 pounds to about 2.160 pounds.

The general symmetry of the present fixation structures simplifies modification to alter the pull-out force for a particular application. The pull-out force can be increased or decreased by adjusting the radial dimension, axial dimension, the number of fixation structures, or a combination thereof. A therapy delivery element with the present fixation structures preferably exhibit a pullout-force from the living body in a range of between about 0.50 pounds to about 3.00 pounds.

FIG. 7D illustrates the therapy delivery element 102 with the introducer 104 fully withdrawn. Tension force 132 can be applied to proximal end 134 to remove the therapy delivery element 102 from the patient. As the therapy delivery element 102 is displaced in removal direction 122, edge surfaces 120 of the fixation elements 110 either cut through the surrounding tissue, fold inward toward the therapy delivery element 102, or a combination thereof. The edge surfaces 120 typically have a surface area of engagement with the tissue of about the radial dimension 120 times the thickness of the fixation structures 110.

Figure 8C:
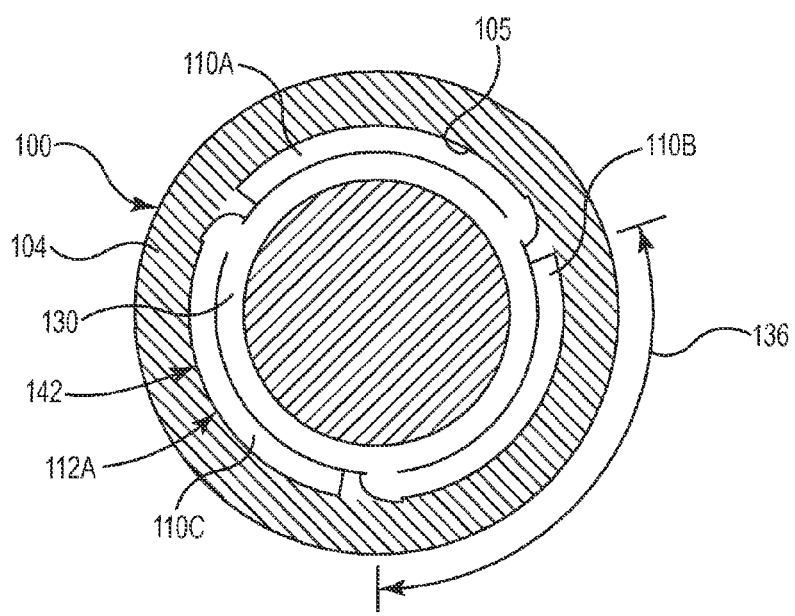
FIG. 8C is a sectional view of the therapy assembly of FIG. 7B with the fixation structures in a collapsed configuration in accordance with an embodiment of the present disclosure.

FIG. 8C is a sectional view of the therapy assembly 100 of FIG. 7B. The fixation assembly 112A is retained within the introducer 104 in collapsed configuration 142 in accordance with an embodiment of the present disclosure. The fixation structures 110A, 110B, 110C collapse radially inward and wrap circumferentially around the therapy delivery element 102 and/or sleeve 130 as the therapy delivery element 102 is inserted into the lumen of the introducer 104. In the preferred embodiment, the surgeon rotates the therapy delivery element 102 as it is being inserted into the lumen 105 of the introducer 104 in order to facilitate the fixation structures 110 wrapping circumferentially as shown in FIG. 8C.

The fixation structures 110A, 110B, 110C preferably follow the contour of the sleeve 130 (or the therapy delivery element 102 when no sleeve 130 is used), but preferably do not overlap in order to minimize the diameter of the therapy assembly 100. Overlapping can be avoided by adjusting the number of fixation structures 110 and the radial dimension 120 of the fixation structures 110.

Figure 8D:
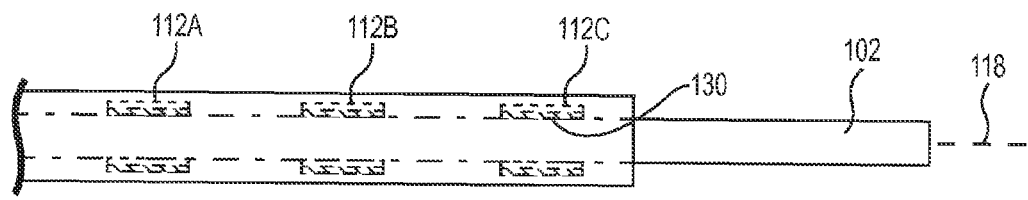
FIG. 8D is a longitudinal sectional view of the therapy assembly of FIG. 7B.

FIG. 8D is a section side view of the therapy assembly 100 of FIG. 8A with the fixation assemblies 112A, 112B, 112C in the collapsed configuration 142. The fixation structures 112 wrap around the sleeve 130 as discussed above.

FIGS. 9A and 9B illustrate axially oriented fixation structures 150A, 150B, 150C ("150") attached to a therapy delivery element 152 in accordance with an embodiment of the present disclosure. Major surfaces 154 on the fixation structures 150 are generally parallel to longitudinal axis 156 of the therapy delivery element 152. The fixation structures 150 optionally include holes 158 to promote tissue in-growth. Promoting tissue in-growth increases the force 132 required to remove the therapy delivery element 152 from the patient.

Proximal edge surfaces 160 and distal edge surfaces 162 are generally perpendicular to the central axis 156 and have about the same surface area. The fixation structures 150 are generally symmetrical so that each proximal edge surface 160 has an opposing distal edge surface 162 with about the same surface area. As a result, the fixation structures 150 provide generally symmetrical resistance to displacement of the therapy delivery element 152 in either proximal direction 164 or the distal direction 166 along the central axis 156. The present fixation structures 110 provide bi-directional axial fixation using opposite edge 160, 162 surfaces of a single structure.

FIGS. 10A and 10B illustrate alternate axially oriented fixation structures 170A, 170B, 170C ("170") attached to a therapy delivery element 172 in accordance with an embodiment of the present disclosure. Portion 174 of the sleeve 176 is removed so that proximal ends 178 of the fixation structures 170 are not attached to the therapy delivery element 172. The proximal ends 178 are free to shift with proximal end 180 of the therapy delivery element 172, such as during active movement by the patient. The free-floating proximal ends 178 act as strain relief for the fixation structures 170, reducing the risk of displacing the therapy delivery element 172.

Edge surfaces 182, 184 are generally perpendicular to the central axis 186 and have about the same surface area. The proximal ends 178, however, also tend to fold toward the major surfaces of the fixation structures 170 in direction 188 during removal of the therapy delivery element 172 in direction 190, facilitating release of any adhered tissue. When the proximal ends 178 are folded in direction 190, the folded structures 178 approximate the edge surfaces 184 sufficiently to provide generally symmetrical resistance to displacement in either direction along the central axis 186.

FIGS. 11A and 11B illustrate alternate axially oriented fixation structures 200A, 200B, 200C ("200") with tapered edge surfaces 202, 204 in accordance with an embodiment of the present disclosure. The tapered edge surfaces 202, 204 are oriented at angles 206, 208 with respect to central axis 210, respectively. In the illustrated embodiment, the tapered edge surfaces 202, 204 are generally symmetrical, resulting in a generally symmetrical resistance to displacement in either direction along the central axis 210.

In an alternate embodiment, the angles 206, 208 are different and the tapered edge surfaces 202, 204 have different surface areas. Viewed along the central axis 210, however, the effective edge surfaces 202, 204 acting along the central axis 210 are sufficiently similar that the resistance to displacement is about the same in either direction along the central axis 210. As used herein, "effective surface area" refers to a surface area of a fixation structure measured in a plane perpendicular to a central axis of a therapy delivery element.

The fixation structures 200 can be attached to a single sleeve or to multiple discrete sleeves 212A, 212B ("212"). Where discrete sleeves 212 are used, the resulting discrete fixation assembly 214A, 214B can be radially and/or axially offset from one another.

FIGS. 12A and 12B illustrate multiple groups of fixation structures 220A, 220B ("220"), 222A, 222B ("222"), 224A, 224B ("224") attached to a single sleeve 226 in accordance with an embodiment of the present disclosure. The fixation structures 222A, 222B are rotated 90 degrees relative to the fixation structures 220A, 220B, 224A, 224B. The groups of fixation structures 222, 224, 226 are separated by axially spacing 228.

The configuration of the present embodiment increases the number of edge surfaces 230, 232 engaged with the patient's tissue at the implantation site, enhancing bidirectional fixation along central axis 238 of the therapy delivery element 236. At the same time the size of each major surface 234 and the total surface area of the major surfaces 234 are both reduced, with a corresponding decrease in tissue adhesion. For some embodiments, increasing the number of edge surfaces 230, 232, while reducing the total surface area of the major surfaces 234 on the fixation structures 222, 224, 226 is the optimum balance of fixation while minimizing tissue adhesion.

FIGS. 13A and 13B illustrate multiple discrete axially oriented fixation assemblies 240A, 240B, 240C ("240") each with a plurality of tapered fixation structures 242 in accordance with an embodiment of the present disclosure. Tapered edge surfaces 244, 246 operate as discussed herein. As best illustrated in FIG. 13B, the discrete fixation assemblies 240 permit rotational positioning around central axis 248 to be offset, increasing the number of active edge surfaces 244, 246 interacting with the tissue.

FIGS. 14A and 14B illustrate multiple discrete fixation assemblies 250A, 250B, 250C ("250") with no axial spacing and pointed fixation structures 252 in accordance with an embodiment of the present disclosure. The proximal and distal edge surfaces 254, 256 are tapered with respect to central axis 258 of the therapy delivery element 260. The tapered edge surfaces 254, 256 operate to reduce the required removal force 132, while providing generally symmetrical resistance to displacement in either direction along the central axis 258, as discussed herein.

FIG. 15 is a side view of a therapy delivery element 262 with fixation assembly 264 having edge surfaces 266A, 266B ("266") that angle inward to create undercuts 268 in accordance with an embodiment of the present disclosure. The proximal edge surfaces 266A are generally equivalent to the distal edge surfaces 266B in terms of surface area and shape, resulting in generally symmetrical fixation of the therapy delivery element 262 along central axis 270, while the undercuts 268 provide enhanced fixation.

FIG. 16 is a side view of a therapy delivery element 280 with hybrid edge surfaces 282A, 282B ("282") and 284A, 284B ("284") in accordance with an embodiment of the present disclosure. Edges 282 provide undercuts 286, while edges 284 are generally perpendicular to central axis 288.

Due to the undercuts 286, the opposing edge surfaces 282A and 284B have different surface areas, as do opposing edge surfaces 284A and 282B. The sum of the proximal edge surfaces 282A, 284A, however, are generally equivalent to the sum of the distal edge surfaces 282B, 284B in terms of surface area and shape, resulting in generally symmetrical fixation of the therapy delivery element 280 along central axis 288.

Figure 17:
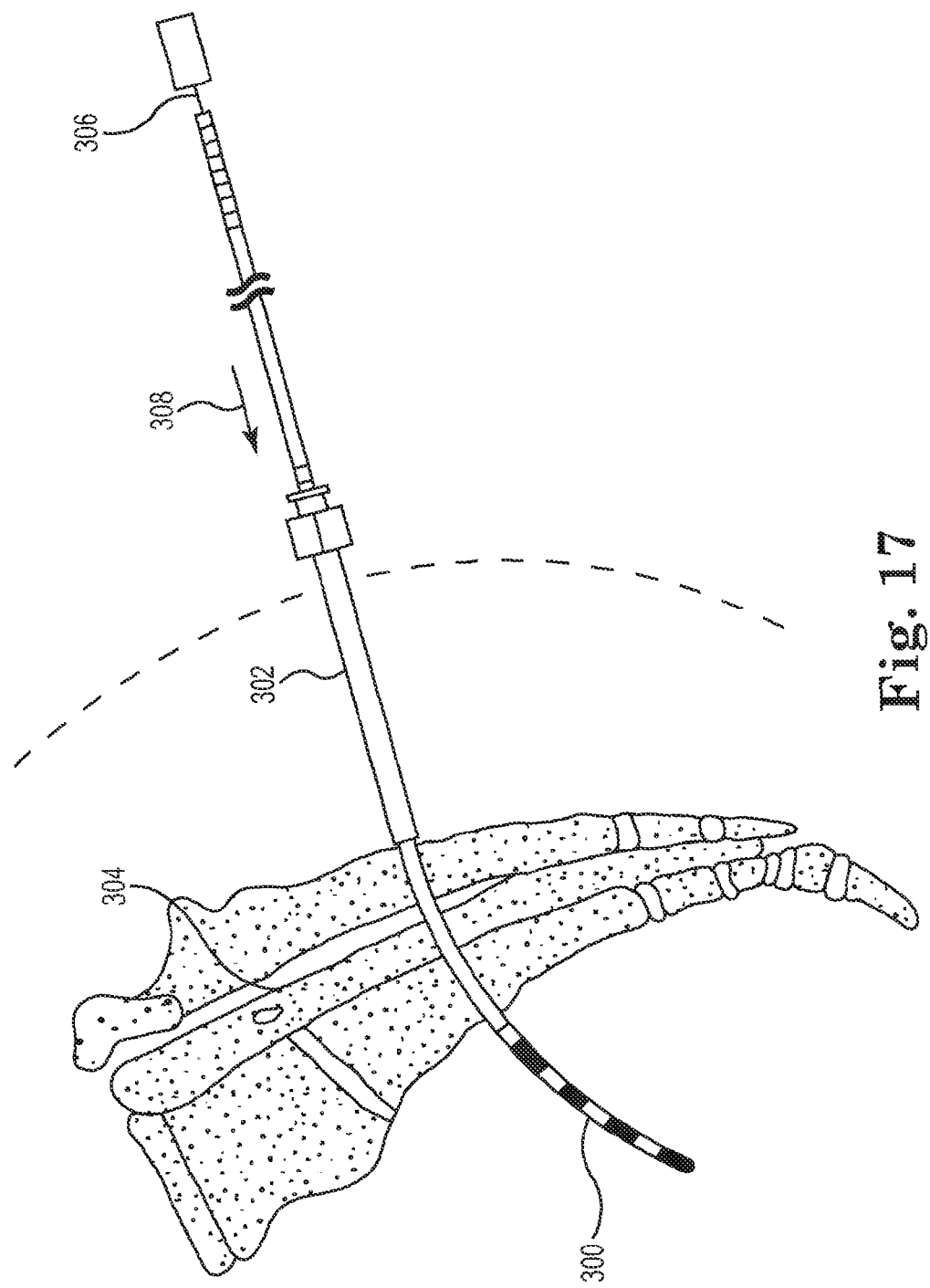
FIG. 17 illustrates a portion of a method of implanting a therapy delivery element in accordance with an embodiment of the present disclosure.

FIG. 17 illustrates one embodiment of implanting a therapy delivery element 300 through introducer 302 in sacral nerve in accordance with an embodiment of the present disclosure. In one embodiment, therapy delivery element 300 is advanced percutaneously at a selected angle through the introducer 302 disposed at the selected foramen 304. The therapy delivery element 300 may be inserted near any of the sacral nerves including the S1, S2, S3, or S4, sacral nerves accessed via the corresponding foramen depending on the necessary or desired physiologic response. Stylet 306 is optionally located in the therapy delivery element 300 to increase stiffness and column strength.

In one embodiment, the introducer 302 is advanced in direction 308 over a guide wire previously percutaneously advanced from the skin incision into the foramen to establish the angle of advancement. In yet another embodiment, a multi-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately result in the therapy delivery element 300 at the location of FIG. 17.

Figure 18:
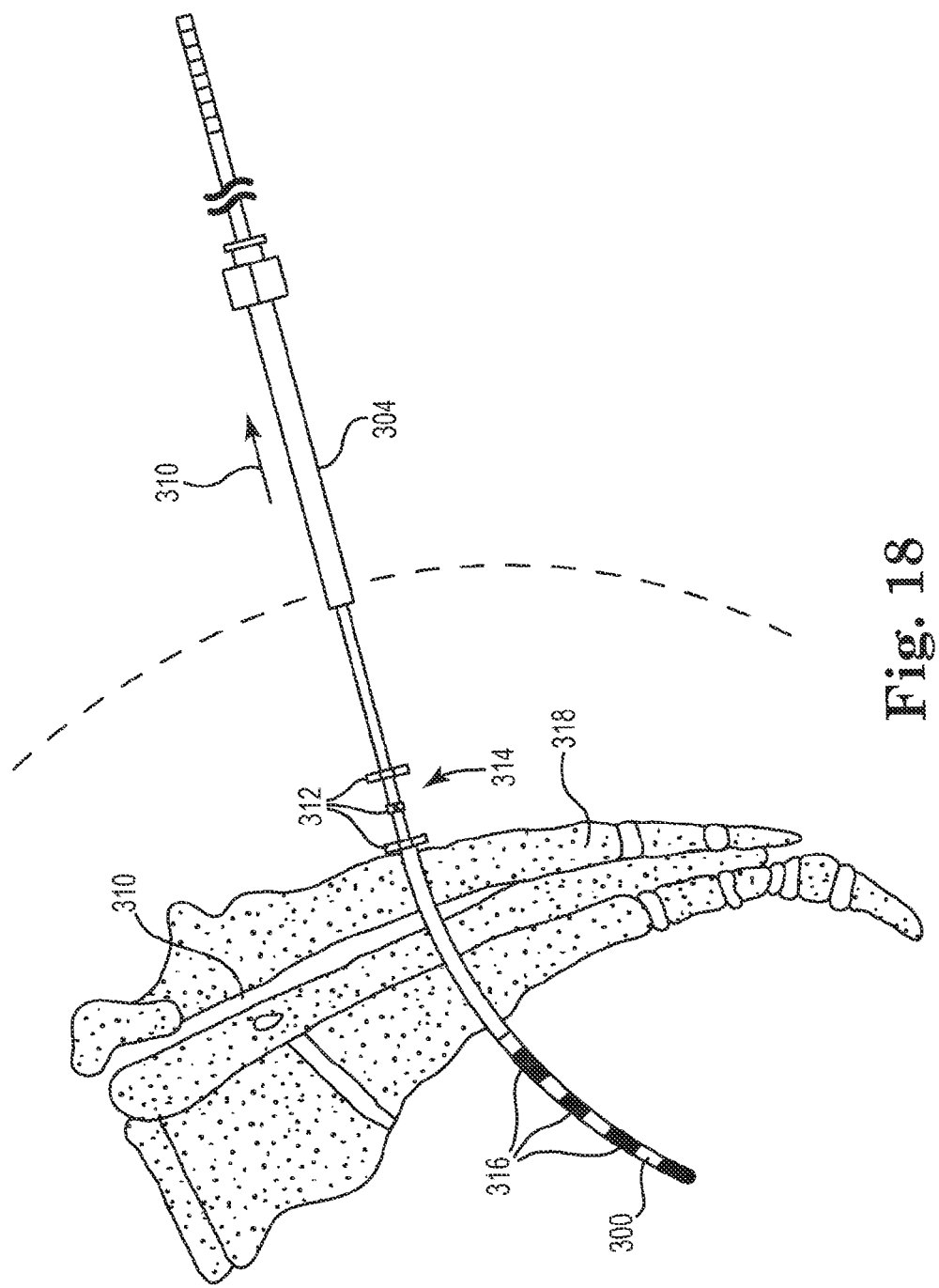
FIG. 18 illustrates a portion of a method of implanting a therapy delivery element in accordance with an embodiment of the present disclosure.

As illustrated in FIG. 18, once nerve mapping is completed and the therapy delivery element 300 is in the desired location, the introducer 302 is retracted proximally in direction 310. The fixation structures 312 are released from the introducer 302 and engage with surrounding subcutaneous tissue 314 to secure the electrodes 316 relative to the foreman 310. In the illustrated embodiment, the fixation structures 312 are axially offset to increase the chance that at least one fixation structure 312 will engage with the muscle tissue located along rear surface of the sacrum 318. In one embodiment the fixation structures 312 can be seen under fluoroscopy to allow the physician to verify that the fixation structures 312 are deployed.

Figure 19:
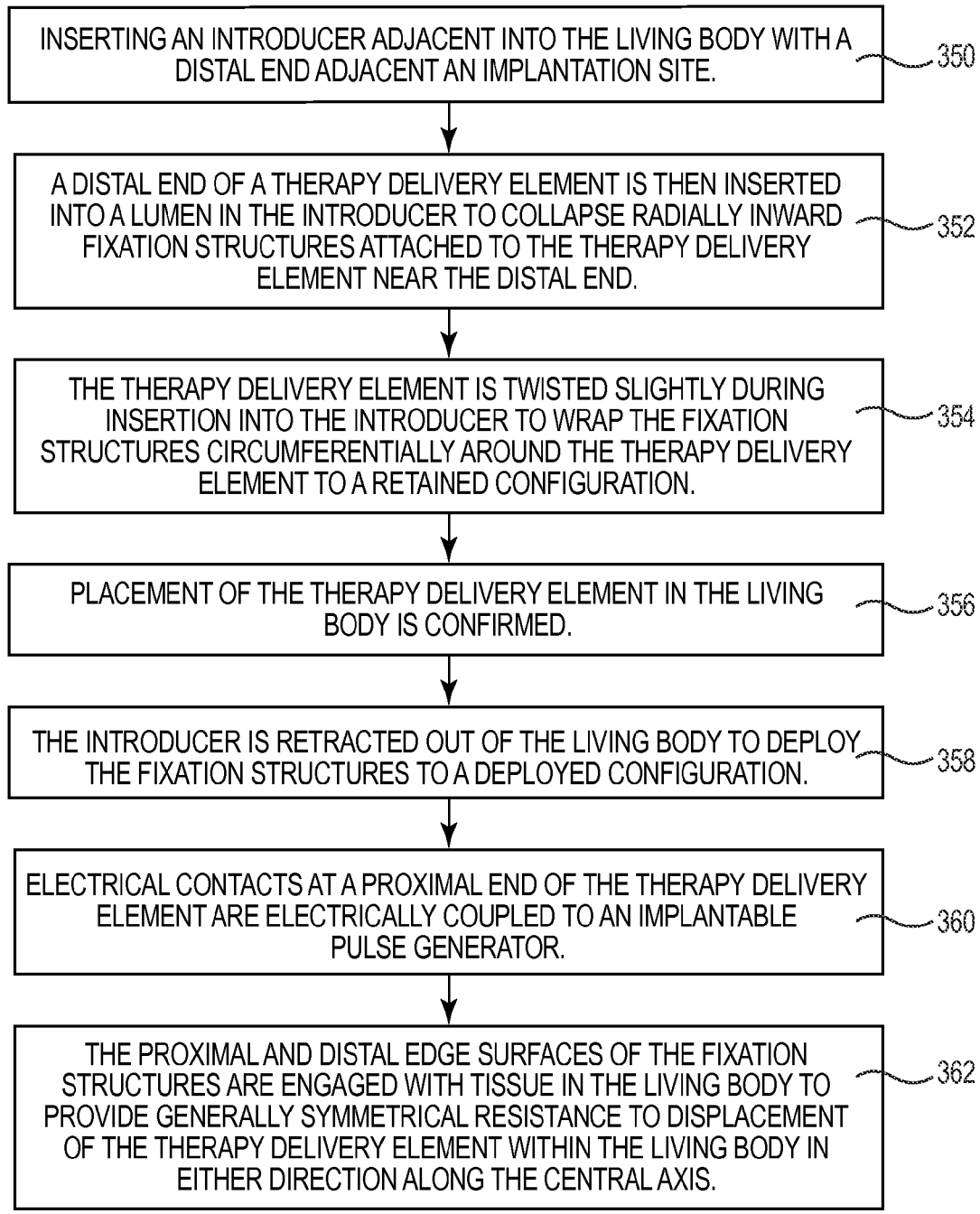
FIG. 19 is a flow chart of steps for implanting a therapy delivery element in accordance with an embodiment of the present disclosure.

FIG. 19 is a flow chart outlining one method of implanting a therapy assembly in a living body. The method includes inserting an introducer adjacent into the living body with a distal end adjacent to an implantation site (350). A distal end of a therapy delivery element is then inserted into a lumen in the introducer to collapse radially inward fixation structures attached to the therapy delivery element near the distal end (352). The therapy delivery element is rotated slightly during insertion into the introducer to wrap the fixation structures circumferentially around the therapy delivery element to a collapsed configuration (354). Placement of the therapy delivery element in the living body is confirmed (356). The introducer is retracted from the living body to deploy the fixation structures to a deployed configuration (358). The fixation structures include major surfaces generally parallel with, and extending radially outward from a central axis of the therapy delivery element, a proximal edge surface oriented toward the proximal end of the therapy delivery element, and a distal edge surface oriented toward the distal end of the therapy delivery element. Electrical contacts at a proximal end of the therapy delivery element are electrically coupled to an implantable pulse generator (360). The proximal and distal edge surfaces of the fixation structures are engaged with tissue in the living body to provide generally symmetrical resistance to displacement of the therapy delivery element within the living body in either direction along the central axis (362).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A therapy assembly configured for at least partial insertion in a living body, comprising:
   a therapy delivery element comprising a proximal end having a plurality of electrical contacts configured to electrically couple with an implantable pulse generator and a distal end having a plurality of electrodes electrically coupled to the electrical contacts;
   an introducer comprising a lumen configured to receive the therapy delivery element therein; and
   a plurality of fixation structures attached to the therapy delivery element proximate from the electrodes, the plurality of fixation structures being configured to collapse radially inward and wrap circumferentially around the therapy delivery element into a collapsed configuration in a non-overlapping configuration when inserted into the lumen, and further being configured to deploy in a deployed configuration when the introducer is retracted from therearound, the plurality of fixation structures comprising major surfaces generally parallel with, and extending generally radially outwardly from, a central axis of the therapy delivery element, a proximal edge surface of the fixation structures being oriented towards the proximal end, a distal edge surface of the fixation structures being oriented towards the distal end;
   wherein the proximal and distal edge surfaces are configured to provide generally symmetrical resistance to displacement of the therapy delivery element in either a proximal direction or a distal direction along the central axis when the therapy delivery element is implanted within the living body.

2. The therapy assembly of claim 1, comprising a plurality of fixation assemblies arranged axially along the therapy delivery element, wherein each fixation assembly comprises at least one of the plurality of fixation structures.

3. The therapy assembly of claim 2, wherein each fixation assembly comprises a plurality of the fixation structure structures, at least two of the fixation assemblies rotationally offset so the proximal and distal edge surfaces of the fixation structures on at least two fixation assemblies are out-of-plane.

4. The therapy assembly of claim 2, wherein the fixation assemblies comprise an axial spacing is in a range between about zero inches to about 0.150 inches.

5. The therapy assembly of claim 1, wherein the fixation structures comprise a radial dimension in a range between about 0.045 inches to about 0.065 inches, and an axial dimension in a range of about 0.050 inches to about 0.200 inches.

6. The therapy assembly of claim 1, wherein the fixation structures comprise a pullout-force from the living body in a range of between about 0.50 pounds to about 3.00 pounds.

7. The therapy assembly of claim 1, wherein at least one of the plurality of fixation structures is bonded directly to the therapy delivery element.

8. The therapy assembly of claim 1, wherein at least one of the plurality of fixation structures is integrally formed into a sleeve that is bonded to the therapy delivery element.

9. The therapy assembly of claim 1, wherein the plurality of fixation structures comprises at least four proximal edge surfaces and four distal edge surfaces.

10. The therapy assembly of claim 1, wherein the proximal edge surfaces comprise a total surface area within about +/−20% or less than a total surface area of the distal edge surfaces.

11. The therapy assembly of claim 1, wherein the plurality of fixation structures comprises a resistance to a displacement force applied to the therapy delivery element in the proximal direction is within about +/−20% or less to resistance to a displacement force applied in the distal direction.

12. A neurostimulation system comprising:
an implantable pulse generator;
a therapy delivery element comprising a proximal end having a plurality of electrical contacts configured to electrically couple with the implantable pulse generator and a distal end having a plurality of electrodes electrically coupled to the electrical contacts;
an introducer comprising a lumen configured to receive the therapy delivery element therein; and
a plurality of fixation structures attached to the therapy delivery element proximate from the electrodes, the fixation structures being configured to collapse radially inward and wrap circumferentially around the therapy delivery element into a collapsed configuration in a non-overlapping configuration when inserted into the lumen, and further being configured to deploy in a deployed configuration when the introducer is retracted from therearound, the plurality of fixation structures comprising major surfaces generally parallel with, and extending generally radially outwardly from, a central axis of the therapy delivery element, a proximal edge surface of the fixation structures being oriented towards the proximal end, a distal edge surface of the fixation structures being oriented towards the distal end;
wherein the proximal and distal edge surfaces are configured to provide generally symmetrical resistance to displacement of the therapy delivery element in either a proximal direction or a distal direction along the central axis when the therapy delivery element is implanted within the living body.

13. The neurostimulation system of claim 12, comprising a plurality of fixation assemblies arranged axially along the therapy delivery element, wherein each fixation assembly comprises at least one of the plurality of fixation structures.

14. The neurostimulation system of claim 13, wherein each fixation assembly comprises a plurality of the fixation structures, at least two of the fixation assemblies rotationally offset so the proximal and distal edge surfaces of the fixation structures on at least two fixation assemblies are out-of-plane.

15. The neurostimulation system of claim 12, wherein at least one of the plurality of fixation structures is bonded directly to the therapy delivery element.

16. The neurostimulation system of claim 12, wherein at least one of the plurality of fixation structures is integrally formed into a sleeve that is bonded to the therapy delivery element.

17. A therapy assembly for at least partial insertion in a living body, the therapy comprising:
a therapy delivery element including:
a proximal end including at least one electrical contact configured to electrically couple with an implantable pulse generator; and
a distal end including at least one electrode electrically coupled to the at least one electrical contact;
an introducer including a lumen configured to receive the therapy delivery element therein; and
at least two or more fixation structures attached to the therapy delivery element proximate the distal end, the at least two or more fixation structures including a proximal edge surface oriented toward the proximal end and a distal edge surface oriented toward the distal end, wherein the at least two or more fixation structures include:
a collapsed configuration in which the at least two or more fixation structures wrap circumferentially around the therapy delivery element but not overlapping one another with insertion of the therapy delivery element into the lumen; and
a deployed configuration in which the at least two or more fixation structures expands radially outwardly from the therapy delivery element with the introducer retracted from the at least one fixation structure, wherein, in the deployed configuration, the proximal and distal edge surfaces are configured to provide substantially symmetrical resistance to displacement of the therapy delivery element in either a proximal direction or a distal direction along the central axis with the therapy delivery element is implanted within the living body.

18. The therapy assembly of claim 17, wherein the at least two or more fixation structures includes major surfaces generally parallel with, and extending generally radially outwardly from, a central axis of the therapy delivery element.

19. The therapy assembly of claim 18, comprising at least two fixation assemblies arranged axially offset from one another along the therapy delivery element, wherein each fixation assembly includes at least two of the fixation structures, and wherein the at least two fixation assemblies are rotationally offset from one another so the major surfaces of the fixation structures on at least two fixation assemblies are out-of-plane from one another.

* * * * *